United States Patent [19]

Soya et al.

[11] Patent Number: 5,334,507

[45] Date of Patent: Aug. 2, 1994

[54] COMPOSITION FOR MEASUREMENT OF POTASSIUM ION CONCENTRATION AND COMPOSITION FOR ELIMINATION OF AMMONIUM IONS

[75] Inventors: Yoshihiro Soya, Shinichi Teshima, Shigenori Emi, all of Tsuruga, Japan

[73] Assignee: Toyo Boseki Kabushiki Kaisha, Osaka, Japan

[21] Appl. No.: 942,579

[22] Filed: Sep. 9, 1992

[30] Foreign Application Priority Data

Sep. 20, 1991 [JP] Japan .................................. 3-270248
Oct. 17, 1991 [JP] Japan .................................. 3-298211

[51] Int. Cl.⁵ ............................ C12Q 1/26; C12Q 1/32
[52] U.S. Cl. ............................................. 435/25; 435/4; 435/12; 435/14; 435/15; 435/19; 435/26
[58] Field of Search ................... 435/4, 12, 14, 15, 19, 435/25, 26

[56] References Cited

U.S. PATENT DOCUMENTS

| | | | |
|---|---|---|---|
| 4,189,536 | 2/1980 | Green | 435/12 |
| 4,490,465 | 12/1984 | Limbach et al. | 435/14 |
| 4,547,461 | 10/1985 | Esdero et al. | 435/25 X |
| 4,608,335 | 8/1986 | Fossati | 435/25 X |
| 4,705,749 | 11/1987 | Willnow et al. | 435/15 |
| 4,767,712 | 8/1988 | Misaki et al. | 435/235 |
| 4,812,400 | 3/1989 | Steinman | 435/25 X |
| 4,818,691 | 4/1989 | Artiss et al. | 435/25 X |
| 4,923,796 | 5/1990 | Deneke et al. | 435/15 |
| 5,037,738 | 8/1991 | Lamos et al. | 435/15 |

FOREIGN PATENT DOCUMENTS

| | | |
|---|---|---|
| 0286039 | 10/1987 | European Pat. Off. . |
| 0348826 | 1/1990 | European Pat. Off. . |
| 3614470 | 11/1986 | Fed. Rep. of Germany . |
| 3731876 | 3/1989 | Fed. Rep. of Germany . |
| WO88/08137 | 10/1988 | PCT Int'l Appl. . |

OTHER PUBLICATIONS

Berry et al., Clinical Chemistry, *Enzymatic Determination of Potassium in Serum*, vol. 35, No. 5, May 1989.
Chang et al., Trans. Am. Soc. Artif. Intern. Organs, *Artificial Cells Microencapsulated Multienzyme System for Converting Urea and Ammonia to Amono Acid Using Ketoglutarate and Glucose as Substrate*, vol. XXIV, 1978.

*Primary Examiner*—Michael G. Wityshyn
*Assistant Examiner*—C. Sayala
*Attorney, Agent, or Firm*—Leydig, Voit & Mayer

[57] ABSTRACT

There is disclosed a composition for measurement of potassium ion concentration, which contains a) pyruvate kinase, b) glycerol kinase, c) glycerol-3-phosphate oxidase, d) peroxidase, e) a chromogen of reduced type, f) adenosine diphosphate or a salt thereof, and g) phosphoenolpyruvic acid or a salt thereof. Also disclosed is a composition for elimination of ammonium ions, which contains a) glutamate dehydrogenase, b) glucose dehydrogenase, and c) nicotinamide adenine dinucleotide of reduced type (NADH) or nicotinamide adenine dinucleotide phosphate of reduced type (NADPH).

23 Claims, 4 Drawing Sheets

COMPOSITION FOR MEASUREMENT OF POTASSIUM ION CONCENTRATION AND COMPOSITION FOR ELIMINATION OF AMMONIUM IONS

FIELD OF THE INVENTION

The present invention relates to a composition for measurement of potassium ion concentration. The measurement of potassium ion concentration in a body fluid is of great significance from the clinical point of view, because it provides useful information on nephropathy (e.g., acute renal failure, chronic renal failure) and endocrinopathy (e.g., primary aldosteronism, secondary aldosteronism).

The present invention also relates to a composition for elimination of ammonium ions, and more particularly, to a composition for elimination of ammonium ions which is useful to measure the concentration of a specified ingredient with high accuracy and precision, for example, in the measurement system capable of producing ammonium ions, such as urea nitrogen and creatinine, or in the measurement system of monovalent metal cations, by elimination of endogenous or exogenous ammonium ions which are responsible for positive errors in the measurement.

BACKGROUND OF THE INVENTION

For the concentration measurement of metal ions such as potassium ions, various methods have hitherto been employed, such as flame photometry, chemical analysis and ion-selective electrode method. However, the flame photometry requires complicated procedures and has a poor capacity for sample processing. The chemical analysis also requires complicated procedures and the reagents to be used therein are expensive, so that it is not actually used in the field of clinical examination. The ion-selective electrode method, although it can be conducted by relatively simple procedures, has the disadvantage that the occurrence of errors in the measurement may be caused by deterioration of the electrode.

In recent years, there are several reports on a method for measurement of potassium ion concentration according to an enzymatic technique. For example, a colorimetric method has been reported in which pyruvate oxidase is allowed to act on pyruvates which are produced by a reaction using pyruvate kinase and the resulting hydrogen peroxide is utilized for forming a quinoid dye under the coexistence of a chromogen and peroxidase, followed by a colorimetric analysis. However, this method is readily affected by endogenous pyruvates and pyruvate oxidase is only available at a high cost, thereby making it difficult to apply this method to commercial use.

In another method disclosed in Clin. Chem., vol. 35, No. 5, pp. 817-820, 1989, a decrease in absorbance is measured at the ultraviolet region (around 340 nm) of nicotinamide adenine dinucleotide of reduced type (NADH), and therefore, this method has the disadvantages that a decrease in the amount of NADH during the storage of reagents makes impossible the measurement of specimens having the possibility of exhibiting high measured values and that the improvement in sensitivity cannot be attained over a certain constant level because a decrease in absorbance is utilized therein. Moreover, as means for avoiding the influence of ammonium ions, glutamate dehydrogenase is usually used to eliminate these ammonium ions according to the scheme I as shown below. This results is another problem that the setting of absorbance or wavelength is difficult when ammonium ions of high concentration should be eliminated, because the wavelength range for measurement of potassium ion concentration overlaps with that for measurement of ammonium ion elimination and a great amount of co-enzymes is required to eliminate ammonium ions of high concentration Scheme I $$\alpha\text{-Ketoglutaric acid} + NH_3 \xrightarrow[NADH \quad NAD]{\text{Glutamate dehydrogenase}} \text{Glutamic acid}$$

Further reported is a method for elimination of ammonium ions by use of glutamine synthetase and asparagine synthetase or by a combination of glutamate dehydrogenase and isocitrate dehydrogenase ("Rinsho-Kensa; Kiki-Shiyaku (Clinical Examination; Equipments and Reagents)", vol. 14, No. 2, April 1991). In the former method, however, glutamine or asparagine produced by the elimination reaction of ammonium ions has a tendency to give free ammonium ions. In the latter method, isocitric acid as a substrate of isocitrate dehydrogenase is too expensive to provide its reagent at a low cost when this method is applied to commercial use. Moreover, the addition of a metal chelating agent is required to terminate the reaction of isocitrate dehydrogenase, but when the concentration of metal ions is measured the addition of a metal chelating agent should be limited to the smallest possible extent because of its negative influence on the measurement. It is, therefore, difficult for these methods to find commercial applications to the measurement of metal ion concentration.

OBJECTS OF THE INVENTION

Under these circumstances, the present inventors have intensively studied a method for measurement of potassium ion concentration in a specimen by use of an enzyme capable of being activated with potassium ions, and found that the amount of adenosine nriphosphate produced in the reaction using pyruvate kinase can be determined by use of glycerol kinase, glycerol-3-phosphate oxidase and peroxidase.

In addition, the present inventors have intensively studied a method for enzymatic elimination of ammonium ions, and found that ammonium ions of low concentration can be effectively eliminated by use of glutamate dehydrogenase. It has also been found that ammonium ions of high concentration cannot be eliminated by only use of glutamate dehydrogenase and the addition of NADH or NADPH of high concentration is required to completely eliminate ammonium ions of high concentration. However, the presence of NADH or NADPH of high concentration has a negative influence on the reaction system with color development using peroxidase, thereby making it impossible to attain sufficient sensitivity. Also, in a method for measurement of the concentration of a specified ingredient in a biological sample by utilization of oxidation and reduction using dehydrogenase, the absorbance at a wavelength for measurement is increased by the presence of NADH or NADPH of high concentration over the measuring range of the spectrophotometer used, thereby making impossible the measurement.

Further studies have led to the finding that NADH or NADPH oxidized in the reaction using glutamate dehydrogenase can be utilized again for the reaction using glutamate dehydrogenase by its reduction using glucose dehydrogenase. That is, the reaction system for effective elimination of ammonium ions of high concentration using NADH or NADPH of low concentration by recycling of NADH or NADPH has been accomplished.

Moreover, it has been found that the incorporation of this reaction system for elimination of ammonium ions into the above system for measurement of potassium ion concentration gives an improvement in the accuracy of the measurement of potassium ion concentration.

It is an object of the present invention to provide a composition for enzymatic measurement of potassium ion concentration, which is excellent in the operating and determining characteristics, as well as in the degree of accuracy and precision.

It is another object of the present invention to provide a composition for enzymatic elimination of ammonium ions, which can be conducted by simple procedures at a low cost.

These objects as well as other objects and advantages of the present invention will become apparent to those skilled in the art from the following description.

SUMMARY OF THE INVENTION

According to the present invention, there is provided a composition for measurement of potassium ion concentration, which comprises a) pyruvate kinase, b) glycerol kinase, c) glycerol-3-phosphate oxidase, d) peroxidase, e) a chromogen of reduced type, f) adenosine diphosphate or a salt thereof, and g) phosphoenolpyruvic acid or a salt thereof.

There is also provided a composition for elimination of ammonium ions, which comprises a) glutamate dehydrogenase, b) glucose dehydrogenase, and c) nicotinamide adenine dinucleotide of reduced type (NADH) or nicotinamide adenine nucleotide phosphate of reduce type (NADPH).

Further provided a combination of the above composition for measurement of potassium ion concentration and the above composition for elimination of ammonium ions.

DETAILED DESCRIPTION OF THE INVENTION

The following will describe a composition for measurement of potassium ion concentration according to the present invention.

The pyruvate kinase to be used herein is not particularly limited to any source, and for example, those obtained from the muscles of rabbit or cattle may be used. Preferred are those derived from the muscles of rabbit. The glycerol kinase to be used herein is also not particularly limited to any source, and for example, those derived from *Candida mycoderma* or *Cellulomans sp.* are used. Preferred are those derived from Cellulomonas sp. The glycerol-3-phosphate oxidase to be used herein is not particularly limited to any source, and those derived from microorganisms are preferably used. The peroxidase to be used herein is not particularly limited to any source, and those derived from horseradish are preferably used.

The chromogen of reduced type to be used herein is not particularly limited. Examples of the chromogen of reduced type are combinations of a coupler (e.g., 4-aminoantipyrine, 3-methyl-2-benzothiazolinone hydrazone) and a phenol derivative (e.g., phenol, 2-chlorophenol, 4-chlorophenol, 2,4-dichlorophenol) or an aniline derivative (e.g., aniline, N,N-dimeEhyl-m-anisidine, N-ethyl-N-(3-methyl-phenyl)-N'-acetylethylenediamine, N-ethyl-N-($\beta$-hydroxyethyl)-m-toluidine, N-ethyl-N-(hydroxy-3-sulfopropyl)-m-toluidine, N-ethyl-N-sulfopropyl-m-toluidine, N-ethyl-N-sulfopropyl-3,5-dimethoxyaniline, N-ethyl-N-(2-hydroxy-3-sulfopropyl)-3,5-dimethoxyaniline, N-ethyl-N-sulfopropyl--m-anisidine, N-ethyl-N-(3-methylphenyl)-N'-succinylethylenediamine, N-ethyl-N-(2-hydroxy-3-sulfopropyl)-m-anisidine). Also, lueco dyes (e.g., 10-N-methylcarbamoyl-3,7-dimethylamino-10H-phenothiazine, bis[3-bis(4-chlorophenyl)methyl-dimethylaminophenyl]amine, 4,4-bis(dimethylamino)diphenyl(2,7-dihydroxy-l-naphthyl)methane) can be used.

The adenosine diphosphate and phosphoenol pyruvic acid to be used herein may be in the form of a salt which is not particularly limited, so long as it contains no potassium ions. Exemplified are their sodium salts, tris(hydroxymethyl)aminomethane salts and cyclohexylamine salts.

The above composition of the present invention may be formulated into a reagent having a pH adjusted by the addition of a buffer to pH 6 to 9. As the buffer to be used herein, those which contain no potassium ions can be used. Examples of the buffer are triethanolamine buffer, Good's buffer and tris buffer.

The above composition of the present invention may further contain any surfactant, preservative, stabilizer and enzyme activator. Preferred examples of the surfactant are nonionic surfactants. Preferred examples of the preservative are NaN$_3$ and antibiotics. The stabilizer and enzyme activator are not particularly limited, so long as they have their own effects. Exemplified are albumin, flavin adenine dinucleotide (FAD) and magnesium ions.

The concentration of pyruvate kinase to be used in a composition for measurement of potassium ion concentration are not particularly limited, so long as it is suitable for the measurement. Preferably used is a concentration in the range of from 0.01 to 10 $\mu$/ml. The glycerol kinase is preferably used at a concentration in the range of from 0.05 to 50 $\mu$/ml. The glycerol-3-phosphate oxidase is preferably used at a concentration in the range of from 0.1 to 50 $\mu$/ml. The peroxidase is preferably used at a concentration in the range of from 1 to 100 $\mu$/ml. The chromogen of reduced type, adenosine diphosphate or a salt thereof, and phosphoenolpyruvic acid or a salt thereof are used at respective concen- trations suitable for the measurement, which are not particularly limited. The chromogen of reduced type is preferably used at a concentration in the range of from 0.01 to 10 mM. The adenosine diphosphate or a salt thereof is preferably used at a concentration in the range of from 1 to 20 mM. The phosphoenolpyruvic acid or a salt thereof is preferably used at a concentration in the range of 0.5 to 5 mM.

Using the above composition of the present invention, the concentration of potassium ions can be measured, for example, according to the following reaction scheme.

Scheme 2
(Measurement system for potassium ions)

Scheme 3 wherein PEP denotes phosphoenolpyruvic acid, GK glycerol kinase, ADP adenosine diphosphate, G3POD glycerol-3-phosphate oxidase, ATP adenosine triphosphate, POD peroxidase, 4-AA 4-aminoantipyrine, G1DH glutamate dehydrogenase, α-KG α-ketoglutaric acid, GLDH glucose dehydrogenase and PK pyruvate kinase.

As described above, a sample is reacted with the reagent containing pyruvate kinase, glycerol kinase and glycerol-3-phosphate oxidase to form $H_2O_2$ which is utilized for forming a quinoid dye under the coexistence of a chromogen and peroxidase, followed by a colorimetric analysis.

The conditions for measurement of potassium ion concentration using the above composition of the present invention are not particularly limited to strict ones. The reaction temperature is usually used in the range of from 10° to 40° C. with preferred being 25° C. or 37° C. The reaction time is preferably used in the range of not more than 10 minutes. The measurement is desirably conducted at a wavelength near the $k_{max}$ of the color-developed dye.

The following will describe a composition for elimination of ammonium ions according to the present invention.

The glutamate dehydrogenase to be used herein is not particularly limited to any source, and for example, those derived from bacteria, yeast or livers of cattle are used. Preferred are those derived from bacteria. The glucose dehydrogenase to be used herein is not particularly limited to any source, and those derived from microorganisms are preferably used. The nicotinamide adenine dinucleotide of reduced type (NADH) and nicotinamide adenine dinucleotide phosphate of reduced type (NADPH) to be used herein are not particularly limited.

The above composition of the present invention may be formulated into a reagent having a pH preferably adjusted by the addition of a buffer to pH 6 to 9. Examples of the buffer are triethanolamine buffer, Good's buffer, tris buffer and borate buffer.

The above composition of the present invention may further contain any surfactant, preservative, stabilizer and enzyme activator. Preferred examples of the surfactant are nonionic surfactants. Preferred examples of the preservative are $NaN_3$ and antibiotics. The stabilizer and enzyme activator are not particularly limited, so long as they have their own effects. Exemplified are albumin, flavin adenine dinucleotide (FAD) and magnesium ions.

The glutamate dehydrogenase and glucose dehydrogenase are used at respective concentrations suitable for the measurement, which are not particularly limited. The glutamate dehydrogenase is preferably used at a concentration in the range of from 20 to 200 μ/ml and the glucose dehydrogenase is preferably used at a concentration in the range of from 10 to 100 μ/mi. The nicotinamide adenine dinucleotide of reduced type (NADH) and nicotinamide adenine dinucleotide phosphate of reduced type (NADPH) are used at respective concentrations suitable for the measurement, which are not particularly limited but preferably in the range of from 0,005 to 0.5 HuM.

The composition for elimination of ammonium ions according to the present invention is employed in various methods for measurement of biological ingredients; for example, methods for measurement with ammonium ions utilized as an reaction intermediate, such as those of urea nitrogen using urease and those of creatinine using creatinine deiminase, or methods for measurement of the concentration of monovalent metal cations such as potassium ions and sodium ions.

The composition for elimination of ammonium ions may be used in combination with the composition for measurement of potassium ion concentration. This combination makes an improvement in the accuracy of the measurement of potassium ion concentration using the latter composition, because ammonium ions can be effectively eliminated by the former composition, even if they are of high concentration. These compositions may be beforehand mixed together and used as a one-liquid type reagent, or may be used independently as a two-liquid type reagent.

The following Examples will describe the present invention in detail, but are not to be construed to limit the scope thereof.

EXAMPLE 1

In this example, a composition for measurement of potassium ion concentration was formulated into reagent A and a combination of this composition with a composition for elimination of ammonium ions was formulated into reagent B. The concentration of potassium ions in a sample was measured using the reagents A and B as follows. As a control, the measurement by an electrode method was conducted with the same sample.

Composition of Reagent A 0.1 M Triethanolamine-HCl buffer, pH 7.6
0.1% Triton X-100

Figure 1:
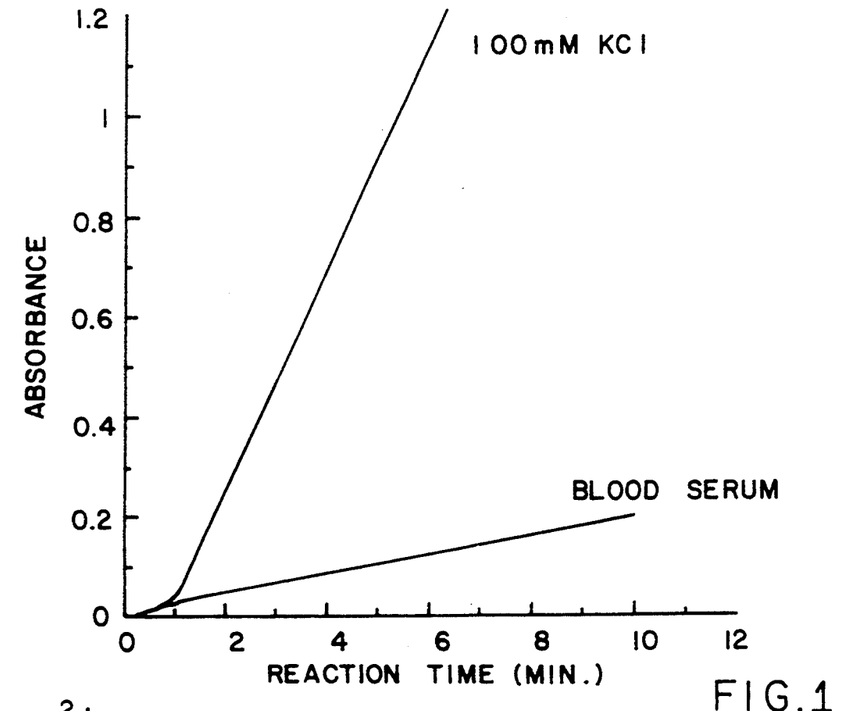
FIG. 1 is a graph showing the time courses of absorbance for the samples of 100 mM KCl and blood serum.
Figure 2:
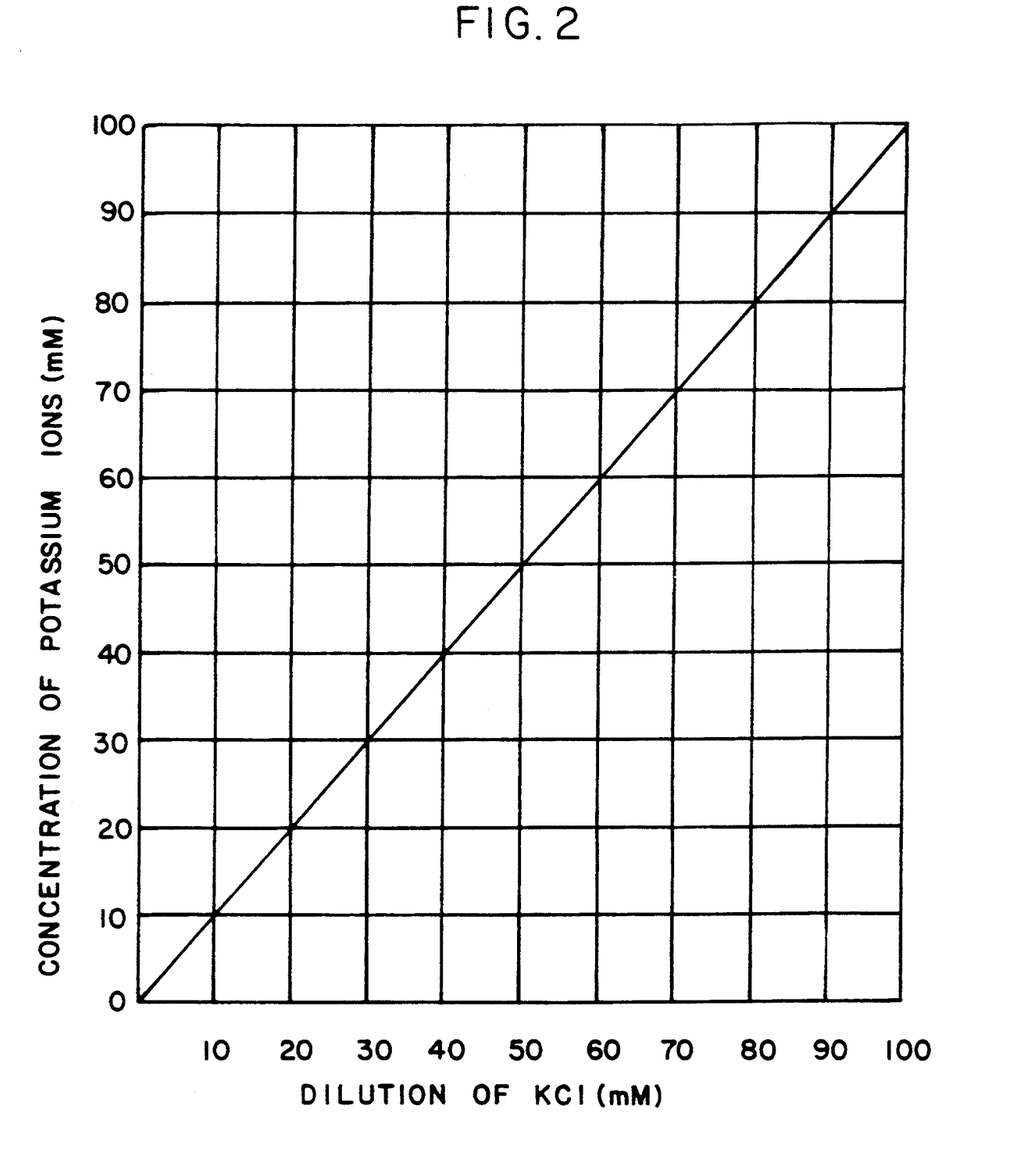
FIG. 2 is a graph showing the linearity in dilution of the samples of 100 nmM KCl
Figure 3:
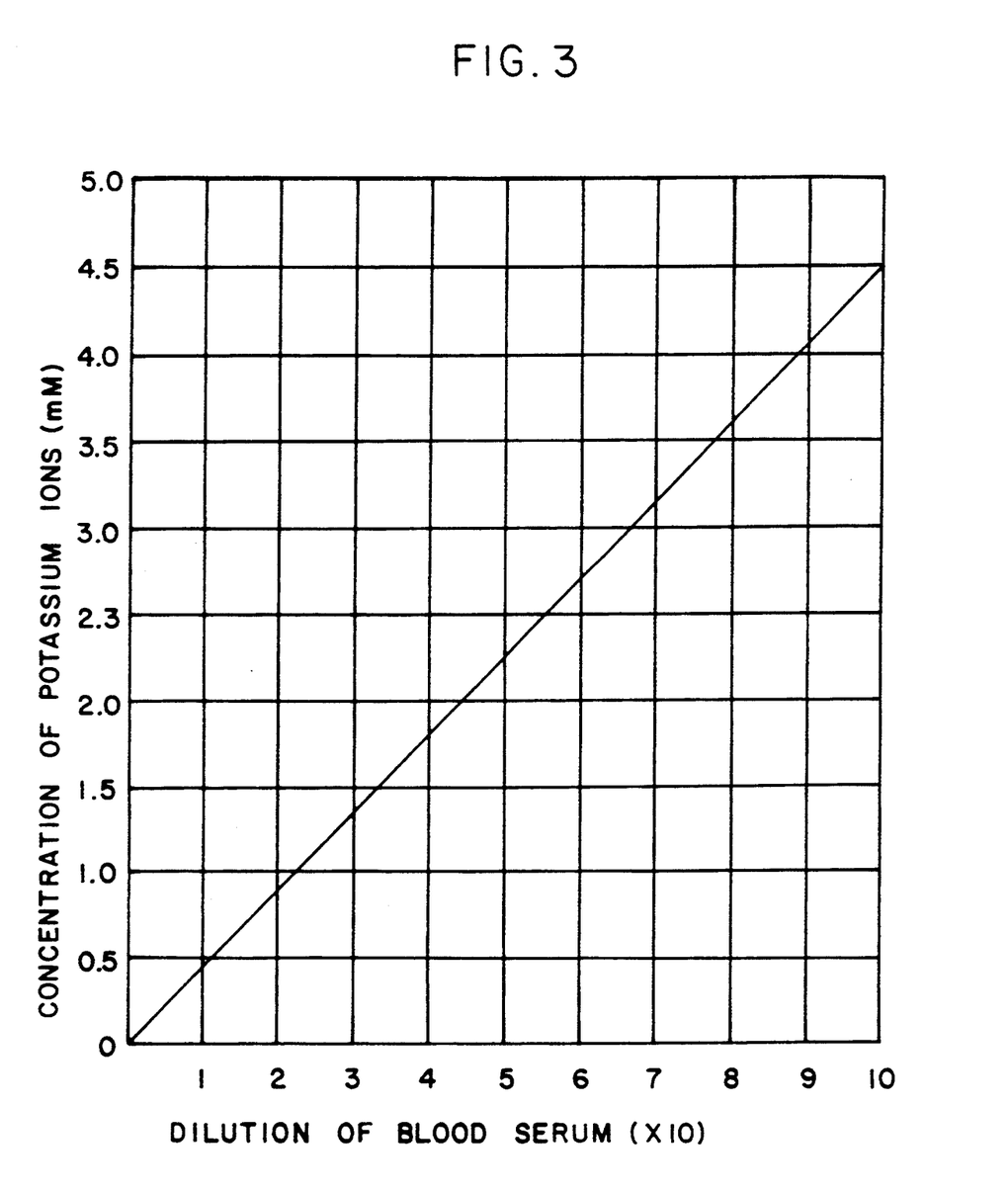
FIG. 3 is a graph showing the linearity in dilution of the samples of blood serum.
Figure 4:
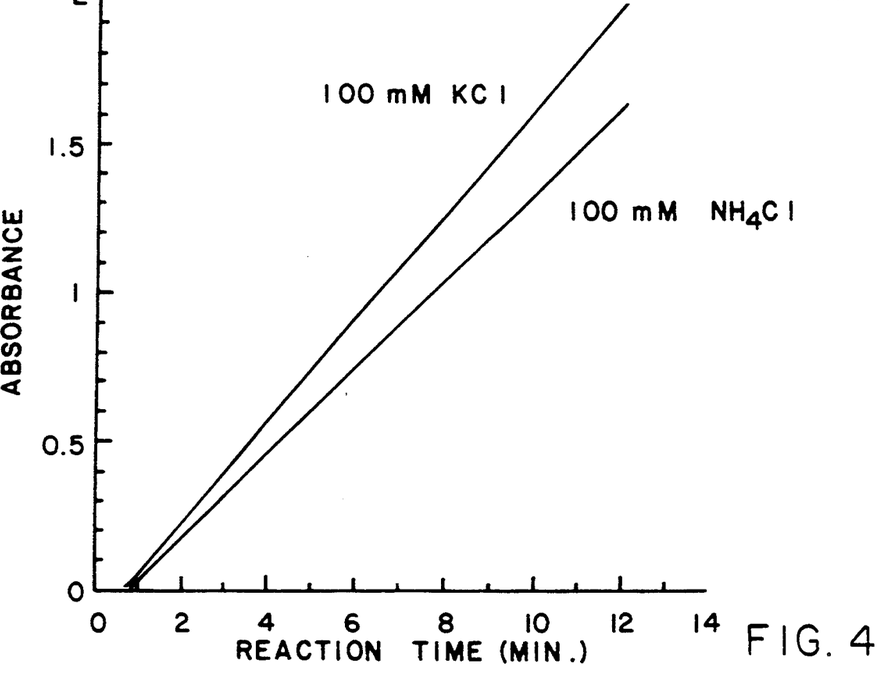
FIG. 4 is a graph showing the time courses of absorbance for the samples of 100 ntM KCl and 100 ntM NH$_4$Cl when the reagent A is used.
Figure 5:
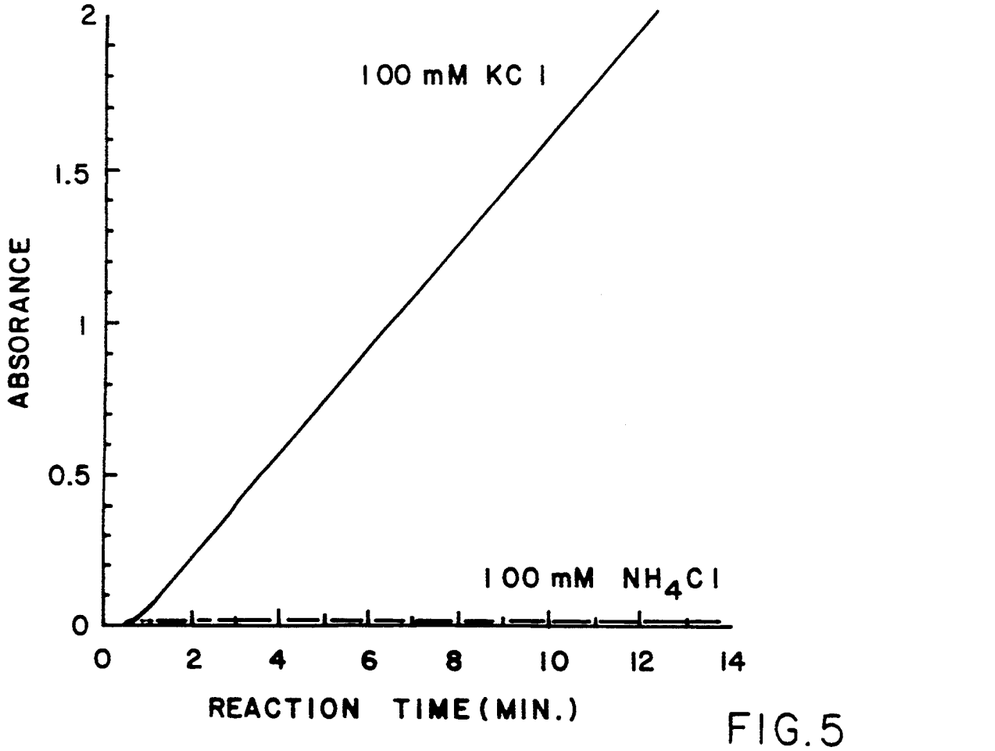
FIG. 5 is a graph showing the time courses of absorbance for the samples of 100 mM KCl and 100 mM NH$_4$Cl when the reagent B is used.

5 him MgCl$_2$
0.2 M Glycerol
4 mM Adenosine triphosphate
0.7 mM Tris salt of phosphoenolpyruvic acid
0.5 mM 4-Aminoantipyrine
2 mM Phenol
0.4 μ/ml Pyruvate kinase
3.0 μ/ml Glycerol kinase
10 μ/ml Glycerol-3-phosphate oxidase
30 μ/ml Peroxidase Composition of Reagent B 0.1 M Triethanolamine-HCl buffer, pH 7.6
0.1% Triton X-100
5 nlM MgCl$_2$
0.2 M Glycerol
4 mM Adenosine triphosphate
0.7 mM Tris salt of phosphoenolpyruvic acid
0.5 mM 4-Aminoantipyrine
2 mM Phenol
0.4 μ/ml Pyruvate kinase
3.0 μ/ml Glycerol kinase
10 μ/ml Glycerol-3-phosphate oxidase
30 μ/ml Peroxidase
50 mM Glucose
5 mM α-Ketoglutaric acid
0.2 mM Nicotinamide adenine nucleotide phosphate of reduced type
50 μ/ml Glutamate dehydrogenase
10 μ/ml Glucose dehydrogenase Measurement Method Serial 10-fold dilutions of 100 mM KCl and serial 10-fold dilutions of blood serum were used as a series of samples. Each of the dilutions was taken at a volume of 40 μl, to which 4 ml of the reagent A or B was added. The mixture was allowed to react at 37° C. for 10 minutes. The time course of absorbance at a wavelength of 400 nm (i.e., the behavior of its enzyme reaction proceeding at the wavelength for measurement) and a change in absorbance for 1 minute were determined. As a blank, distilled water was used instead of the samples containing potassium ions. FIG. 1 shows the time courses of absorbance for the samples of 100 mM KCl and blood serum. FIGS. 2 and 3 show the linearity in dilution of the samples of 100 mM KCl and blood serum, respectively. As can be seen from the figures, the concentration of potassium ions can be simply measured with high accuracy for a short period of time, even when aqueous solutions of potassium chloride and blood serum are used as samples. Further, serial 10-fold dilutions of 100 mM NH$_4$Cl were used as samples for the same measurement as described above. FIGS. 4 and 5 show the time courses of absorbance for the samples of 100 mM KCl and 100 nlM NH$_4$Cl, respectively.

The following Tables 1 and 2 show the results of measurements for the samples using the reagents A or B, or by an electrode method.

TABLE 1

| Sample | Reagent A (mM) | Reagent B (mM) | Electrode Method (mM) |
| --- | --- | --- | --- |
| Distilled water | 0 | 0 | *** |
| 10 mM KCl | 10.0 | 10.0 | 10.0 |
| 20 mM KCl | 19.9 | 20.0 | 20.0 |
| 30 mM KCl | 30.0 | 30.1 | 30.1 |
| 40 mM KCl | 39.8 | 40.1 | 40.1 |
| 50 mM KCl | 50.1 | 50.0 | 50.0 |

TABLE 1-continued

| Sample | Reagent A (mM) | Reagent B (mM) | Electrode Method (mM) |
| --- | --- | --- | --- |
| 60 mM KCl | 60.0 | 59.9 | 59.9 |
| 70 mM KCl | 70.0 | 70.0 | 70.0 |
| 80 mM KCl | 80.1 | 80.0 | 80.0 |
| 90 mM KCl | 90.0 | 90.1 | 90.1 |
| 100 mM KCl | 99.9 | 100 | 100 |
| Neat blood serum | 4.3 | 4.3 | 4.3 |

TABLE 2

| Sample | Reagent A (mM) | Reagent B (mM) | Electrode Method (mM) |
| --- | --- | --- | --- |
| Distilled water | 0 | 0 | *** |
| 10 mM NH$_4$Cl | 7.8 | 0 | *** |
| 20 mM NH$_4$Cl | 15.4 | 0 | *** |
| 30 mM NH$_4$Cl | 23.4 | 0 | *** |
| 40 mM NH$_4$Cl | 30.5 | 0 | *** |
| 50 mM NH$_4$Cl | 39.6 | 0 | *** |
| 60 mM NH$_4$Cl | 47.8 | 0 | *** |
| 70 mM NH$_4$Cl | 55.0 | 0 | 1.0 |
| 80 mM NH$_4$Cl | 62.4 | 0 | 1.2 |
| 90 mM NH$_4$Cl | 70.5 | 0 | 1.4 |
| 100 mM NH$_4$Cl | 77.9 | 0 | 1.5 |
| Neat blood serum | 4.3 | 4.3 | 4.3 |

Table 3 shows the results of measurements for the samples of blood serum with the addition of 100 mM KCl or 100 mM NH$_4$Cl using the reagent A or B, or by an electrode method.

TABLE 3

| Sample | Reagent A (mM) | Reagent B (mM) | Electrode Method (mM) |
| --- | --- | --- | --- |
| Neat blood serum | 4.5 | 4.3 | 4.3 |
| Neat blood serum + 100 mM KCl | 104.6 | 104.3 | 104.3 |
| Neat blood serum + 100 mM NH$_4$Cl | 82.6 | 4.3 | 5.8 |

EXAMPLE 2

In this example, a composition for elimination of ammonium ions was formulated into reagent C. The capacity of eliminating ammonium ions in a sample was determined using the reagent C as follows.

Figure 6:
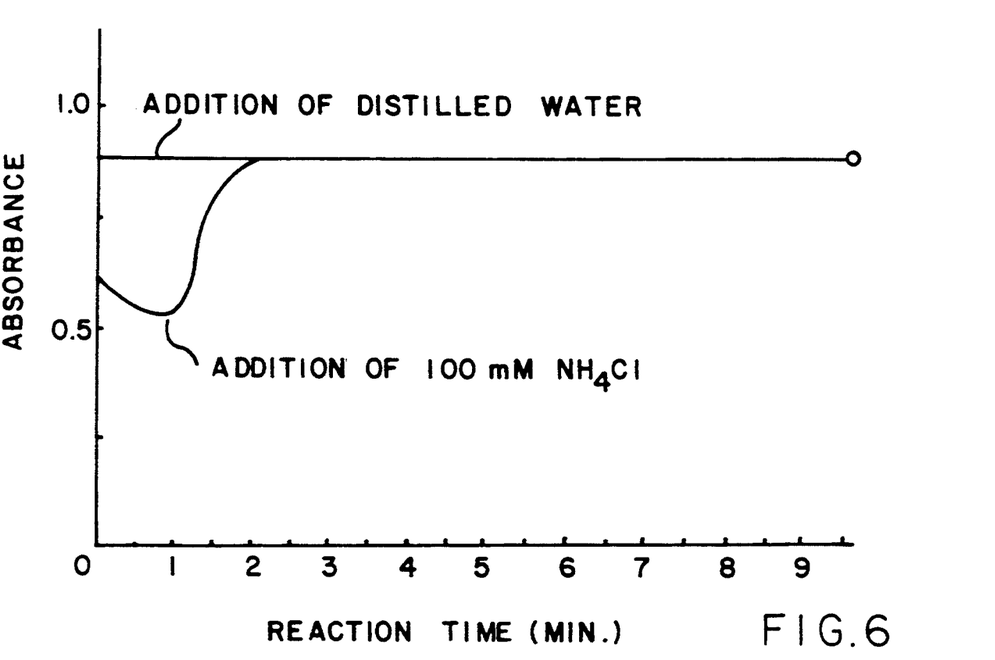
FIG. 6 is a graph showing the time courses of absorbance of the samples of 100 mM KCl and distilled water when the reagent C is used.

Composition of Reagent C 0.1 M Good's buffer, pH 7.5
0.1% Triton X-100
10 mM α-Ketoglutaric acid
0.1 M Glucose
0.2 mM Nicotinamide adenine dinucleotide phosphate of reduced type
50 μ/ml Glutamate dehydrogenase
10 μ/ml Glucose dehydrogenase To 3 ml of the reagent C, 0.05 ml of 100 mM NH$_4$Cl or distilled water was added, and the mixture was subjected to the measurement of absorbance at a wavelength of 340 nm for 10 minutes. The time course of absorbance thus obtained is shown in FIG. 6.

EXAMPLE 3

In this example, a composition for elimination of ammonium ions was formulated into reagents D and E which is for comparison. A controlled blood serum was used as a sample, and the concentration of urea nitrogens in this sample was measured using the reagents D and E as follows.

Composition of Reagent D 0.1 M Good's buffer, pH 7.5
0.1% Triton X-100
10 mM α-Ketoglutaric acid
0.1 M Glucose
0.2 mM Nicotinamide adenine dinucleotide phosphate of reduced type
50 μ/ml Glutamate dehydrogenase
10 μ/ml Glucose dehydrogenase Composition of Reagent E 0.1 M Good's buffer, pH 7.5
0.1% Triton X-100
10 μ/ml Urease
0.01 mM Monoiodoacetate
0.2 mM Nicotinamide adenine dinucleotide phosphate of reduced type To 0.05 ml of a controlled blood serum, 2 ml of the reagent D was added, and the mixture was incubated at 37° C. for 5 minutes. Then, 2 ml of the reagent E was added and the resulting mixture was subjected to the measurement of absorbance at a wavelength of 340 nm for 5 minutes. From a change in the absorbance over 3 to 5 minutes, the concentration of urea nitrogens was determined. As a comparison, the same measurement as described above was conducted, except that the reagent E was not used. These results are shown together in Table 4.

TABLE 4

| Sample | Reagents D and E (mM) | Reagent E only (mM) | Indicated Value (mM) |
|---|---|---|---|
| A | 11.7 | 12.6 | 11.6 |
| B | 28.9 | 35.0 | 28.9 |
| C | 50.3 | 51.7 | 50.2 |
| D | 41.3 | 78.2 | 41.1 |
| E | 13.2 | 16.4 | 13.3 |
| F | 18.8 | 20.1 | 18.8 |

What is claimed is:

1. A composition for measurement of potassium ion concentration, which comprises a) pyruvate kinase, b) glycerol kinase, c) glycerol-3-phosphate oxidase, d) peroxidase, e) a chromogen of reduced type, e) adenosine diphosphate or a salt thereof, and e) phosphoenolpyruvic acid or a salt thereof, said composition being suitable for the measurement of potassium ion concentration.

2. A composition according to claim 1, which comprise a) pyruvate kinase at a concentration of from 0.01 to 10 μ/ml, b) glycerol kinase at a concentration of from 0.05 to 50 μ/ml, c) glycerol-3-phosphate oxidase at a concentration of from 0.1 to 50 μ/ml, d) peroxidase at a concentration of from 1 to 100 μ/ml, e) a chromogen of reduced type at a concentration of from 0.01 to 10 mM, f) adenosine diphosphate or a salt thereof at a concentration of from 1 to 20 mM, and g) phosphoenolpyruvic acid or a salt thereof at a concentration of from 0.5 to 5 mM.

3. A composition for elimination of ammonium ions, which comprises a) glutamate dehydrogenase, b) glucose dehydrogenase, and c) nicotinamide adenine dinucleotide of reduced type (NADH) or nicotinamide adenine dinucleotide phosphate of reduced type (NADPH), said composition being suitable for the elimination of ammonium ions.

4. A composition according to claim 3, which comprises a) glutamate dehydrogenase at a concentration of from 20 to 200 μ/ml, b) glucose dehydrogenase at a concentration of from 10 to 100 μ/ml, and c) nicotinamide adenine dinucleotide of reduced type (NADH) of nicotinamide adenine dinucleotide phosphate of reduced type (NADPH) at a concentration of from 0.005 to 0.5 mM.

5. A combination of a first composition for measurement of potassium ion concentration and a second composition for elimination of ammonium ions, the first composition comprising a) pyruvate kinase, b) glycerol kinase, c) glycerol-3-phosphate oxidase, d) peroxidase, e) a chromogen of reduced type, e) adenosine diphosphate or a salt thereof, and e) phosphoenolpyruvic acid or a salt thereof, and the second composition comprising a) glutamate dehydrogenase, b) glucose dehydrogenase, and c) nicotinamide adenine dinucleotide of reduced type (NADH) or nicotinamide adenine dinucleotide phosphate of reduced type (NADPH), said combination being suitable for the measurement of potassium ion concentration and for the elimination of ammonium ions.

6. A method for the measurement of potassium ion concentration in a body fluid sample, said method comprising reacting said body fluid sample with a composition comprising a) pyruvate kinase, b) glycerol kinase, c) glycerol-3-phosphate oxidase, d) peroxidase, e) a chromogen of reduced type, f) adenosine diphosphate or a salt thereof, and g) phosphoenolpyruvic acid or a salt thereof and thereafter performing a colorimetric analysis.

7. The method according to claim 6, wherein said body fluid sample is a blood serum sample.

8. The method according to claim 6, wherein said pyruvate kinase is in a concentration in said composition from about 0.01 to about 10 μ/ml, said glycerol kinase is in a concentration in said composition from about 0.05 to about 50 μ/ml, said glycerol-3-phosphate oxidase is in a concentration in said composition from about 0.1 to about 50 μ/ml, said peroxidase is in a concentration in said composition from about 1 to about 100 μ/ml, said chromogen is in a concentration in said composition from about 0.1 to about 10 mM, said adenosine diphosphate or salt thereof is in a concentration in said composition from about 1 to about 20 mM, and said phosphoenolpyruvic acid or salt thereof is in a concentration in said composition from about 0.5 to about 5 mM.

9. A method for the elimination of ammonium ions in a body fluid sample, said method comprising reacting said body fluid sample with a composition comprising) glutamate dehydrogenase, b) glucose dehydrogenase, and c) nicotinamide adenine dinucleotide of reduced type (NADH) or nicotinamide adenine dinucleotide phosphate of reduced type (NADPH).

10. The method according to claim 9, wherein said body fluid sample is a blood serum sample.

11. The method according to claim 9, wherein said glutamate dehydrogenase concentration in said composition from about 20 to about 200 μ/ml, said glucose dehydrogenase concentration in said composition from about 10 to about 100 μ/ml, and said NADH or said NADPH concentration in said composition from about 0.005 to about 0.5 mM.

12. A method for the simultaneous elimination of ammonium ions in a body fluid sample and measurement of potassium ion concentration in said body fluid sample, said method comprising reacting said body fluid sample with a composition comprising a) pyruvate kinase, b) glycerol kinase, c) glycerol-3-phosphate oxidase, d) peroxidase, e) a chromogen of reduced type, f) adenosine diphosphate or a salt thereof, g) phosphoenolpyruvic acid or a salt thereof, h) glutamate dehydrogenase, i) glucose dehydrogenase, and j) nicotinamide adenine dinucleotide of reduced type (NADH) or nicotinamide adenine dinucleotide phosphate of reduced type (NADPH) and thereafter performing a colorimetric analysis.

13. The method according to claim 12, wherein said body fluid sample is a blood serum sample.

14. The method according to claim 6, wherein said composition further comprises phenol.

15. The method according to claim 6 wherein said composition further comprises a buffer to maintain a pH of said composition of from about 6 to about 9.

16. The method according to claim 15, wherein said buffer is selected from the group consisting of triethanolamine buffer, Good's buffer and tris buffer.

17. The method according to claim 6, wherein said composition further comprises a preservative.

18. The method according to claim 17, wherein said preservative is selected from the group consisting of $NaN_3$ and antibiotics.

19. The method according to claim 6, wherein said composition further comprises a surfactant.

20. The method according to claim 19, wherein said surfactant is a nonionic surfactant.

21. The method according to claim 6, wherein said composition further comprises a stabilizer and enzyme activator.

22. The method according to claim 21, wherein said stabilizer and enzyme activator is selected from the group consisting of albumin, flavin adenine dinucleotide (FAD) and magnesium ions.

23. The method according to claim 6, wherein said reaction is carried out at from about 10° to about 40° C.

* * * * *

UNITED STATES PATENT AND TRADEMARK OFFICE
CERTIFICATE OF CORRECTION

PATENT NO. : 5,334,507
DATED : AUGUST 2, 1994
INVENTOR(S) : YOSHIHIRO SOYA, SHINICHI TESHIMA AND SHIGENORI EMI

It is certified that error appears in the above-indentified patent and that said Letters Patent is hereby corrected as shown below:

Column 2, line 2, delete "is" and substitute therefor -- in --;

Column 2, line 44, delete "nriphosphate" and substitute therefor -- triphosphate --;

Column 3, line 32, delete "nmM" and substitute therefor -- mM --;

Column 3, line 36, for both occurrences delete "ntM" and substitute therefor -- mM --;

Column 3, line 42, after "100" delete "rnM" and substitute therefor -- mM --;

Column 4, lines 21-22, delete "N,N-dimeEhyl-m-anisidine" and substitute therefor -- N,N-dimethyl-m-anisidine --;

Column 4, line 32, after "methyl-" insert -- 4- --;

Column 5, line 55, delete "kma$_x$" and substitute therefor -- $\lambda_{max}$ --;

Column 6, line 23, delete "$\mu$/mi" and substitute therefor -- $\mu$/ml --;

Column 6, line 29, delete "0,005" and substitute therefor -- 0.005 -- and delete "HuM" and substitute therefor -- mM --;

Column 7, line 1, delete "him" and substitute therefor -- mM --;

Column 7, line 15, delete "nlM" and substitute therefor -- mM --;

Column 7, line 55, delete "nlM" and substitute therefor -- mM --; and

Column 8, line 58, delete "rnM" and substitute therefor -- mM --.

UNITED STATES PATENT AND TRADEMARK OFFICE
CERTIFICATE OF CORRECTION

PATENT NO. : 5,334,507

DATED : AUGUST 2, 1994

INVENTOR(S) : YOSHIHIRO SOYA, SHINICHI TESHIMA AND SHIGENORI EMI

It is certified that error appears in the above-indentified patent and that said Letters Patent is hereby corrected as shown below:

Column 9, lines 53-54, delete "comprise" and substitute therefor -- comprises --;

Column 10, line 7, delete the second occurrence of "of" and substitute therefor -- or --;

Column 10, line 63, after "dehydrogenase" insert -- is in a --;

Column 10, line 65, after "dehydrogenase" insert -- is in a --; and

Column 10, line 67, after "NADPH" insert -- is in a --.

Signed and Sealed this

Twenty-eighth Day of November 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,334,507
DATED : August 2, 1994
INVENTOR(S) : Soya et al.

Page 1 of 2

It is certified that error appears in the above-indentified patent and that said Letters Patent is hereby corrected as shown below:

In Column 4, lines 60, 62, 64, and 66: "µ/ml" should read --U/ml--.

In Column 6, line 23, µ/ml should read --U/ml--.

In Column 6, lines 21 "µ/ml" should read --U/ml--.

In Column 7, line 1, "him" should read --mM--.

In Column 7, lines 7, 8, 9, 10, 21, 22, 23, 24, 29, and 30: "µ/ml" should read --U/ml--.

In Column 8, lines 56 and 57: "µ/ml" should read --U/ml--.

In Column 9, lines 11, 12, 18, 55, 56, 57, and 58: "µ/ml" should read --U/ml--.

In Column 10, lines 5, 6, 40, 42, 44, 46, 64, and 66: "µ/ml" should read --U/ml--.

UNITED STATES PATENT AND TRADEMARK OFFICE
CERTIFICATE OF CORRECTION

PATENT NO. : 5,334,507
DATED : August 2, 1994
INVENTOR(S) : Soya et al.

It is certified that error appears in the above-indentified patent and that said Letters Patent is hereby corrected as shown below:

In Column 7, lines 15 and 55, "NIM" should read --mM--.

Signed and Sealed this

Third Day of December, 1996

Attest:

BRUCE LEHMAN

*Attesting Officer*      *Commissioner of Patents and Trademarks*